United States Patent [19]

Highgenboten

[11] Patent Number: 5,222,115
[45] Date of Patent: Jun. 22, 1993

[54] FILM CASSETTE CARRIER ACCURATE POSITIONING MECHANISM FOR X-RAY APPARATUS AND METHOD

[76] Inventor: Carl L. Highgenboten, 7777 Forest La. #C-106, Dallas, Tex. 75230

[21] Appl. No.: 787,672

[22] Filed: Nov. 4, 1991

[51] Int. Cl.<sup>5</sup> ............................................. G03B 42/02
[52] U.S. Cl. .................................. 378/177; 378/181; 378/182; 378/205; 378/209
[58] Field of Search ............... 378/181, 176, 177, 172, 378/173, 182, 189, 205, 147, 208, 209

[56] References Cited

U.S. PATENT DOCUMENTS

| | | |
|---|---|---|
| 2,567,566 | 9/1951 | Kizaur . |
| 2,840,429 | 6/1958 | McDonald . |
| 2,888,567 | 5/1959 | Land . |
| 2,989,634 | 6/1961 | Ould . |
| 3,040,174 | 6/1962 | Robin . |
| 3,532,882 | 10/1970 | Craig et al. . |
| 3,567,931 | 3/1971 | Eelkema .................. 378/171 |
| 4,031,400 | 6/1977 | Hunt et al. .............. 378/173 |
| 4,152,604 | 5/1979 | Burbury ................... 378/189 |
| 4,205,233 | 5/1980 | Craig et al. ............. 378/209 |
| 4,552,347 | 11/1985 | Wallis ....................... 378/209 |
| 4,916,725 | 4/1990 | Quinter et al. ......... 378/177 |

Primary Examiner—David P. Porta
Assistant Examiner—Kim-Kwok Chu
Attorney, Agent, or Firm—Baker & Botts

[57] ABSTRACT

X-ray apparatus for supporting a patient is provided which comprises a housing having a top panel for supporting the patient and a bottom panel which rests on a table. The top and bottom panels are supported to be substantially parallel and spaced from one another. A frame is mounted in the housing to receive a conventional X-ray film cassette. Drive means is further provided to slidably transporting the frame longitudinally in X-ray apparatus housing. Further means is provided to accurately indicate the position of the frame.

54 Claims, 2 Drawing Sheets

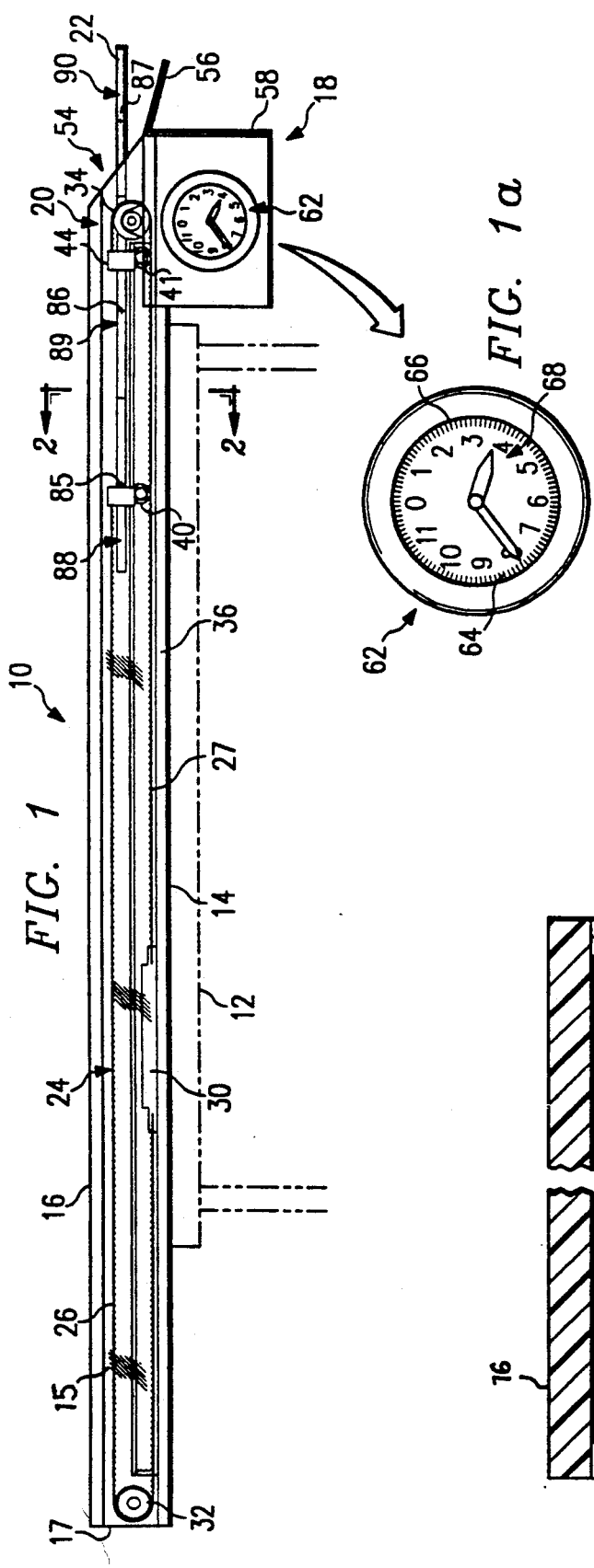

FILM CASSETTE CARRIER ACCURATE POSITIONING MECHANISM IN X-RAY APPARATUS AND METHOD

TECHNICAL FIELD OF THE INVENTION

This invention relates in general to X-ray apparatus and method, and more particularly, to apparatus for accurate positioning of X-ray film cassette under a patient's body and a method for performing the same.

BACKGROUND OF THE INVENTION

In the past, whenever an X-ray is required of a patient who is lying on a hospital bed, cooperation by the patient is necessary to elevate portions of the patient's body so that an X-ray film cassette may be inserted thereunder. This task becomes significantly more difficult or utterly impossible when the patient is immobilized by injury or anesthesia. More particularly, in the course of certain surgical procedures, it may be desirable to obtain X-rays of a fully draped and anesthetized patient to determine the degree of success of the operation so that corrections may be made promptly.

A number of X-ray apparatus have been developed to provide a solution to this problem. For example, U.S. Pat. No. 4,205,233 issued to Craig et al. on May 27, 1980 provides an X-ray table with a slidable bucky tray for carrying an X-ray film which can be moved by manual manipulation through a longitudinal opening in the table. U.S. Pat. No. 3,040,174 issued to Robin on Jun. 19, 1962 describes a device for immobilizing infants for taking X-rays which has a slidable X-ray film tray located beneath the top surface of the device. The tray may be positioned manually through several slot openings in the side of the device. U.S. Pat. 2,567,566 issued to Kizaur on Sep. 11, 1951 describes a slidable X-ray film carriage located beneath the table which may be positioned manually by grasping a handle on the carriage extending through a longitudinal slot and exerting force thereon.

Although the above-described apparatus provides for the ability to furnish an X-ray film beneath the patient, the X-ray film is movable and positionable only by manual manipulation through slots or openings alongside the table, which likely interferes with procedures being performed on the patient in an emergency situation or in the operating room. Additionally, such slots or openings are likely to be rendered inaccessible by the surgical drapes. A number of X-ray apparatus were developed in response to this concern. For example, U.S. Pat. No. 2,888,567 issued to Land on May 26, 1959 shows an X-ray tilt table which includes a film cassette carriage manually movable longitudinally beneath the table by turning a hand crank. The cassette carriage as well as the end of the table have hinged doors for loading and unloading the film cassette. However, a further need in X-ray apparatus has not been satisfactorily addressed.

In certain applications, it is necessary to position the X-ray film cassette and repeatably return the cassette to the same position with some precision. Furthermore, it may be necessary to move and reposition the X-ray film cassette relative to a prior location with some precision. U.S. Pat. No. 4,916,725 issued to Quinter et al. on Apr. 10, 1990 and U.S. Pat. No. 2,989,634 issued to Ould et al. on Jun. 20, 1961 both attempted to offer a solution to the problem of accurate X-ray film positioning. Quinter et al. shows an improved apparatus on the device taught by Ould, both providing an X-ray table with an X-ray film cassette push rod etched with graduations that can be inserted from one end of the table to move the cassette. Quinter et al. additionally provides a graduated scale along the length of the table, so that the film cassette may be moved to a second position relative to the first by looking at the displacement indicated by the graduated scale. Both devices taught by Quinter and Ould are inadequate for a number of reasons. First, by providing a scale along the length of the table, the X-ray technician must operate the push rod from a location at the end of the table and at a location beside the bed for a clear view of the scale. The technician must move between these two locations to position, adjust and readjust the X-ray film cassette. The alternative is to provide a two-person operation where one manipulates the rod and the other visually aligns the film cassette to the measurements on the scale.

Second, when a patient is fully draped or being operated on by medical personnel, it is difficult or impossible to achieve visual contact with the graduated scale for a precise positioning of the film cassette. Third, a typical operating room does not provide sufficient space at the end of the operating table for using the push rod, as the rod must be sufficiently extended horizontally to insert it under the table and to move the film cassette longitudinally. Difficulties arise especially when the film cassette is being pulled to the end of the table to be loaded or unloaded. Therefore, the Quinter and Ould devices are especially unsuitable in an operating room application where the table is under drapes and where there is not sufficient room at the end of the operating table for manipulating the push rod.

Accordingly, it is desirable to provide X-ray apparatus for accurate and repeatable positioning of an X-ray film cassette beneath a patient, especially in an operating room situation where the operating table is under drapes and space is scarce. Furthermore, it is vital that the film cassette is manipulatable and positionable without disturbance or interference with the medical personnel who are performing important medical procedures.

In a particular application, consider a replacement arthroplasty procedure for installing a trial knee prosthetic implant. It is often desirable to check the alignment of the trial knee prosthetic implant with respect to the femoral head of the hip and the ankle during the arthroplasty procedure. In addition to the problem of positioning the film under a fully draped and anesthetized patient, the special problem of taking an X-ray of an extraordinarily large area is also encountered. Typically, a standard full-length (36"×14") X-ray film is used to obtain an X-ray image of the entire leg. However, it is not possible to obtain a full-length X-ray during surgery because of the inability or unfeasibility of positioning such a large film under the patient. Furthermore, even if a full-length X-ray film is somehow positioned under the patient during surgery, the X-ray source often cannot be positioned far enough above the patient to obtain coverage of a full-length film. There is additionally the problem that the full-length film may not be long enough to receive the image of the entire leg in a taller patient.

Therefore, it is desirable to provide a method for taking X-rays to determine the alignment of a certain body part with respect to another without having to use full-length X-ray film.

SUMMARY OF THE INVENTION

In accordance with the present invention, apparatus and a method for accurate positioning of an X-ray film cassette under a patient's body are provided which substantially eliminate or reduce disadvantages and problems associated with prior X-ray apparatus.

In one aspect of the present invention, X-ray apparatus for supporting a patient is provided. The apparatus comprises a housing having a top panel for supporting the patient and a bottom panel which rests on a standard operating room table. The top and bottom panels are supported to be substantially parallel and spaced from one another. A frame is mounted in the housing to receive a conventional X-ray film cassette. Drive means is further provided for slidably transporting the frame longitudinally in the X-ray apparatus housing. Further means is provided to accurately indicate the position of the frame.

In another aspect of the present invention, X-ray apparatus is provided for supporting a patient and use with X-ray equipment. The X-ray apparatus comprises substantially horizontal and elongated top and bottom panels, which define a cavity therebetween. At least one channel is disposed longitudinally within the cavity for receiving the wheels of an X-ray film carrier. The carrier is coupled to a drive system that is adapted for slidably transporting it longitudinally substantially the length of the apparatus. An indicator is further coupled to the drive system for displaying a value indicative of the position of the carrier.

In yet another aspect of the present invention, a method of X-raying a patient is provided. The method includes the steps of actuating a drive mechanism to position an X-ray film cassette beneath a preselected body portion of the patient. The position of the cassette is noted as indicated by a position indicator. The film cassette is repositioned by actuating the drive mechanism again to achieve alignment with another body portion of the patient, and its position is again noted. These steps are repeated until cassette positions corresponding to all preselected body portions are obtained. After the medical procedure is performed, the cassette is positioned at each of the earlier noted positions by actuating the drive mechanism and noting the position thereof, and X-rays are taken at each respective position, only exposing a preselected portion of the X-ray film at each cassette position.

In a further aspect of the present invention, a method of X-raying a patient during an arthroplasty procedure is provided. The method involves the steps of actuating a drive mechanism to position an X-ray film cassette beneath the hips of the patient. The position of the cassette is noted as indicated by a position indicator. The film cassette is repositioned by actuating the drive mechanism again to achieve alignment with the knees and ankles of the patient, and its positions are also noted. During the arthroplasty procedure after the bone cuts are made and while the trial prosthetic implants are in place, the X-ray film cassette is positioned at each of the earlier noted positions by actuating the drive mechanism and noting the position thereof, and X-rays are taken at each respective position, only exposing a preselected portion of the X-ray film at each position, so that a composite image of the hips, knees and ankles are obtained on a single X-ray film.

An important technical advantage of the present invention provides medical personnel the ability to not only position an X-ray film under an immobilized patient, but also the ability to reposition the film with accuracy. This advantage is especially significant in an operating room setting where the patient may be totally immobilized by anesthesia and fully draped for surgery.

A further important technical advantage of the present invention provides a method for assessing the alignment of a trial prosthetic implant during an arthroplasty procedure. Such immediate assessment is significant because it permits the immediate performance of any corrective action if required.

BRIEF DESCRIPTION OF THE DRAWINGS

For a better understanding of the present invention, reference may be made to the accompanying drawings, in which:

FIG. 1 is a simplified side view of a preferred embodiment of the present invention;

FIG. 1a is an enlarged view of the measurement indicator on the turn wheel shown in FIG. 1;

FIG. 2 is a simplified cross-sectional view of the preferred embodiment of the present invention taken along line 2—2 of FIG. 1;

FIG. 3 is a simplified end view of a driving mechanism of the preferred embodiment of the present invention;

DETAILED DESCRIPTION OF THE INVENTION

Figure 4:
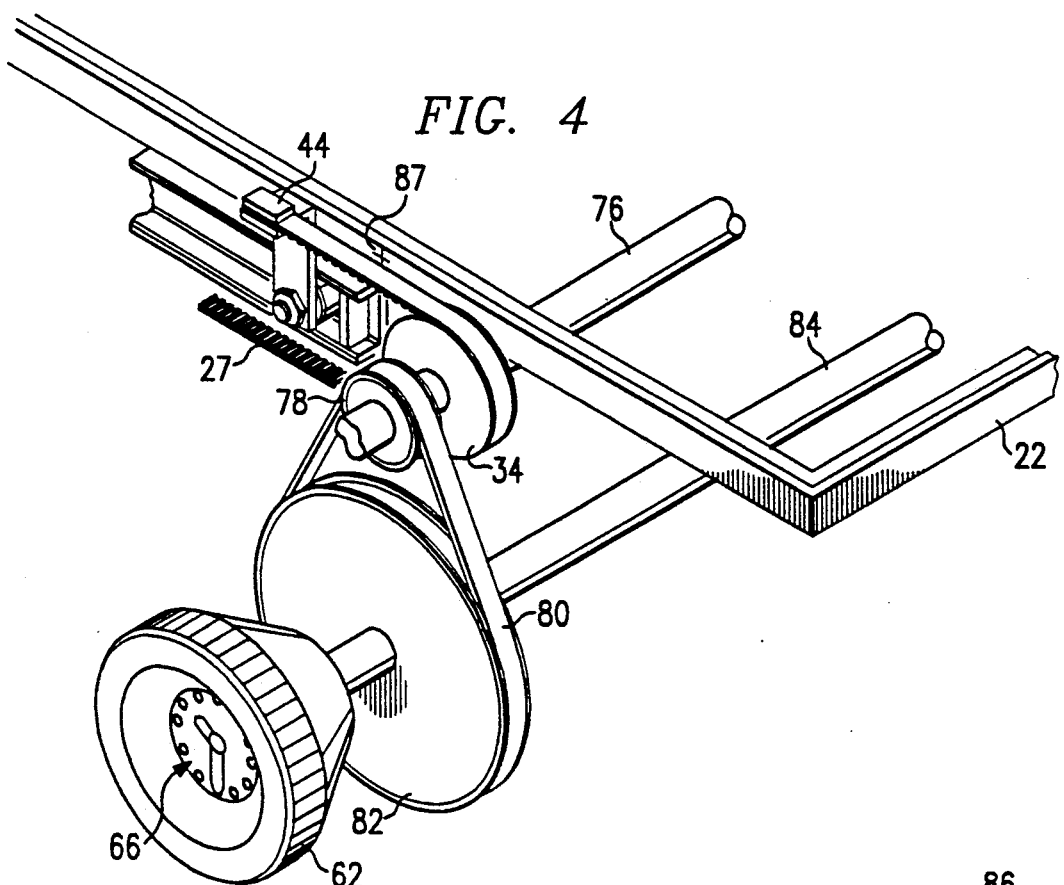
FIG. 4 is a simplified perspective view of the same driving mechanism.

With reference to the drawings, FIG. 1 illustrates a side view of X-ray apparatus, indicated generally at 10 and constructed according to the teaching of the present invention. X-ray apparatus 10 is shown positioned upon an operation table 12, where its bottom panel 14 meets the top surface of the operation table 12. A top panel 16, substantially parallel to bottom panel 14, provides a surface to support a patient. Top panel 16 is constructed from materials which are known to be X-ray transmissive. Top and bottom panels 16 and 14 are preferably joined by generally perpendicular side panels 15, 17 and 19, as shown in FIGS. 1 and 2. Side panels 15, 17 and 19 of apparatus 10, preferably constructed from a transparent material, such as clear Lexan manufactured by General Electric, are arranged to join top and bottom panels 16 and 14. The side panels are preferably perpendicular to top and bottom panels 16 and 14 with the exception of the side wall at the head of apparatus 10, details of which is discussed below. Alternatively top and bottom panels 16 and 14 may be joined by a number of vertical struts or a framework (not shown) to provide clear and visible view of belt drive system 20. A gear box 18 housing a belt drive system 20 for transporting a conventional X-ray film cassette (not shown) longitudinally is arranged at the "head" end of X-ray apparatus 10 opposing "foot" end panel 17. It is well known that an X-ray film cassette is permeable to X-rays and typically contains one X-ray film.

As viewed through the generally transparent side panel of apparatus 10, belt drive system 20 includes an X-ray film cassette carrier or carriage 22 for holding a conventional film cassette (not shown). The preferable film cassette size contemplated in the present invention is fourteen inches by seventeen inches (14"×17"). Carriage 22 is arranged to be driven by belt drive system 20 to slide longitudinally along X-ray apparatus 10. Belt drive system 20 includes a conventional timing belt 24 having two segments 26 and 27. One end of timing belt segment 26 is connected to one end of carriage 22 and the other is connected to a counterweight or belt tensioner 30. Timing belt segment 26 is further wound around a pulley 32 mounted on a transverse pulley rod (not shown) at the "foot" end of X-ray apparatus 10. The structure and mounting of pulley 32 and its pulley rod are conventional and are not described in detail herein. Timing belt segment 27 is also connected to belt tensioner 30 and carriage 22, but is wound around a pulley 34 positioned near gear box 18. Therefore, timing belt segments 26 and 27, belt tensioner 30 and film cassette carriage 22 form a continuous loop around pulleys 32 and 34, extending substantially the entire length of X-ray apparatus 10. Accordingly, when either pulley 32 or 34 is rotated, the rotational displacement of pulleys 32 and 34 is translated to a linear displacement of belt segments 26 and 27. In turn, carriage 22 is displaced linearly along substantially the length of x-ray apparatus 10. Preferably, belt segments 26 and 27 are provided with teeth or cogs for a better interface with pulleys 32 and 34 which preferably have mating cogs or teeth.

Referring also to FIG. 2, the longitudinal displacement of carriage 22 is further guided by a pair of generally C-shaped channels 36 and 37 running longitudinally substantially the entire length of X-ray apparatus 10. The opening of channels 36 and 37 face side panels 15 and 19 respectively or outward from a center longitudinal line (not shown) of X-ray apparatus 10. Channels 36 and 37 form the surface and guide for four carriage wheels 40-42 (one not shown) which are connected to carriage 22 near the four corners and protrude inwardly toward the center of carriage 22. Carriage wheels 40-42 thus ride on the inner lower surface of channels 36 and 37. Carriage wheels 40-42 may be fastened to carriage 22 via plates 44 and 46 which extend downwardly, and are secured thereon by fasteners such as bolts 48 and 49 shown. Accordingly, channels 36 and 37 and wheels 40-41 allow carriage 22 to slide smoothly, easily and consistently along the length of X-ray apparatus.

Returning to FIG. 1, it can be seen that the longitudinal travel of carriage 22 is limited by the length of channels 36 and 37. At the end of its travel at the "head" end of X-ray apparatus 10 near gear box 18, a portion of carriage 22 is allowed to extend out of an end opening 54 for loading and unloading of the X-ray film cassette. Opening 54 may be closed off by a door 56 hinged at its bottom to an end panel 58 of gear box 18. An optional spring resistance may be added to door 56 to further encourage it to stay closed.

The linear displacement of carriage 22 is made possible by belt drive system 20 as described above. Belt drive system 20 includes additional components which link pulley 34 to a manual turn wheel 62. Manual turn wheel 62 may be equipped with a knob (not shown) for ease of manipulation, if preferred. In addition, manual turn wheel 62 may be implemented by like components which serve like functions, such as a hand crank. Manual turn wheel 62 is additionally equipped with an indicator 66 for displaying the amount of carriage travel longitudinally along X-ray apparatus 10. Generally, the indicated amount of displacement is a relative length measurement from a predetermined point along X-ray apparatus 10, such as either end of channels 36 and 37.

As shown in FIG. 1a, indicator 66 preferably includes a circular face having a plurality of large divisions indicated by numerals somewhat like a clock face, and is further divided into finer divisions. A pair of short and long hands 68 are provided for pointing to the rough and fine divisions, respectively. As shown, the face of indicator 66 has 12 divisions and 100 finer divisions. As shown in FIG. 1a, short and long hands 68 in combination indicate a carriage position of 3.67, for example. The reading of 3.67 is obtained from reading the short hand to obtain 3 and reading the long hand to obtain 8, which translates to $8 \times 12/100 = 0.67$. The sum of 3 and 0.67 yields 3.67. Thus, depending on the implementation of apparatus 10, the amount of distance available for carriage travel will dictate the correspondence between the indicator reading and actual distance traveled by carriage 22. For example, if carriage 22 travels 50 cm during the travel of the long hand completely around the face of indicator 66 or the short hand from one large divisions marker to the next, then each large division represents 50 cm of carriage travel and each fine division represents 50/100 cm or 0.50 cm of carriage travel. Accordingly, substantially accurate displacement indication is available to more accurately position and reposition carriage 22 longitudinally at desirable locations. Manual turn wheel 62 with indicator 66 is commercially available, such as one manufactured by Tejax Engineering Co. in Pawtucket, R.I.

Referring jointly to FIGS. 3 and 4 for an end view and a perspective view of a portion of apparatus 10, the linkage between pulley 34 and manual turn wheel 62 is shown in more detail. Pulley 34, which is coupled to carriage 22, is arranged to turn about a transverse pulley rod 76. Pulley rod 76 is mounted through the center of pulley 34 and is further connected to a pulley 78 having a generally smaller circumference than pulley 34. Wound around pulley 78 is another belt 80. Belt 80 also extends around a drive pulley 82. Drive pulley 82 is mounted on a drive rod 84 that is mounted transversely with respect to the carriage 22. Drive pulley 82 and manual turn wheel 62 are both mounted on the drive rod 84.

In operation, when manual turn wheel 62 is caused to rotate by manual manipulation, in a clockwise direction for example, drive rod 84 is caused to rotate, which in turn causes drive pulley 82 to rotate in a clockwise direction. The clockwise rotation of drive pulley 82 causes belt 80 to force pulley 78 to also turn in a clockwise direction, which causes pulley rod 76 and pulley 34 to turn in response. The clockwise rotation of pulley 34 then causes carriage 22 to travel along channels 36 and 37 toward end opening 54. It can be seen that to cause carriage 22 to travel toward the opposite end, manual turn wheel 62 is turned in a counterclockwise direction, which reverses the rotation of pulleys 34 and 82.

It may be easily seen that other means of driving mechanism for actuating the longitudinal travel of carriage 22 is contemplated. For example, motorized belt drive systems or other electrical means may be used to affect carriage travel. In addition, electrical or electronic sensory means disposed on or along channels 36 and 37 may be employed to detect the position of carriage 22, and an electronic read out used to display the detected position. The implementation of X-ray apparatus 10 with such alternate means is contemplated by the present invention and is constrained only by the economic feasibility of such implementations.

The operation of X-ray apparatus 10 is better illustrated in the application to operating rooms. Immediately prior to surgery, a patient is placed on X-ray apparatus 10 and procedures are taken to prepare and anesthetize the patient for surgery. At or prior to this time, an operator may visually align X-ray film cassette carriage 22 under the portion of the patient's body that will require X-rays by looking through transparent side panels 15 or 19 of X-ray apparatus 10. The operator can make note of the position of carriage 22 by ascertaining its relative position as indicated by indicator 66. The operator may perform this procedure a number of times if X-rays of multiple body parts are required. Subsequently, the patient is anesthetized and fully draped for surgery. During or immediately before and after certain procedures in the course of surgery, if an X-ray of the patient is desired, the operator is able to position X-ray film cassette carriage 22 according to earlier noted positions by manipulating manual turn wheel 62 so that the desired reading is shown by indicator 66. Therefore, position and alignment of carriage 22 can be performed without disturbing the surgical drapes and without substantial interference to the operating staff. X-ray film carriage 22 can then be repositioned elsewhere along apparatus 10 exposed after film has been removed and new film has been loaded.

Figure 5:
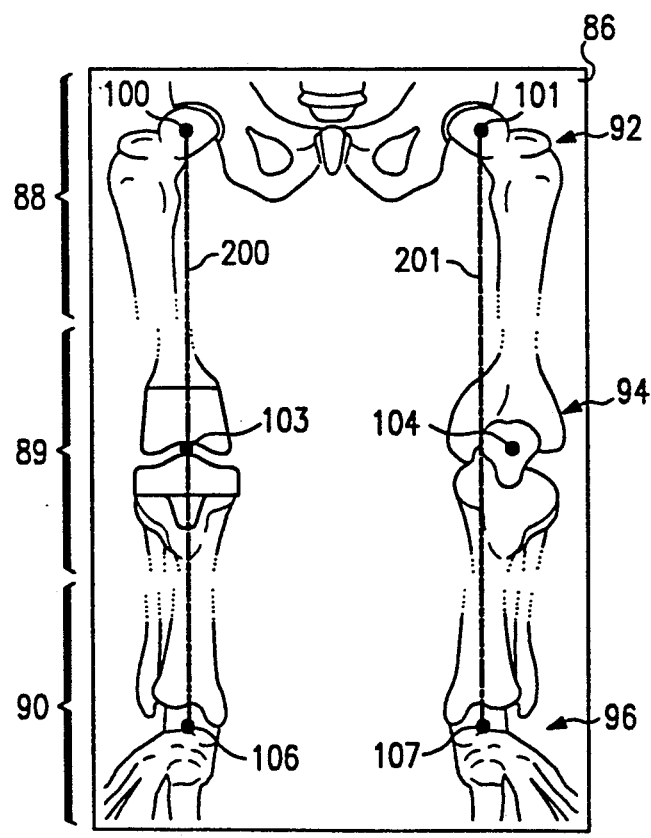
FIG. 5 is a line drawing representation of a composite X-ray image obtained by a particular preferred method of operation of the present invention.

Referring to FIG. 5, a special application method of X-ray apparatus 10 is illustrated. The application method, according to the present invention, targets those instances where multiple X-rays of a patient is desirable during and/or immediately after surgery. In particular, the present method addresses the need to determine whether a trial knee prosthetic implant installation procedure is successful, so that corrective steps may be performed if required.

The success of the arthroplasty procedure can be determined by the alignment of the trial knee prosthetic implant with respect to the patient's hip or the center of the femoral head and the patient's ankle of the same leg. The conventional assessment method of alignment made outside the operating room is done by taking a full length (36"×14") X-ray of the patient's leg or legs. A line is drawn on the developed X-ray image between the center of the femoral head and the center of the ankle. If the line falls medially (towards the inside edge of the knee) or laterally (towards the outside edge of the knee) excessively, then the prosthetic implant is improperly aligned. However, as discussed above, it is impossible to obtain a full-length X-ray in the operating room setting.

It is proposed by the present inventive method to divide a 14"×17" X-ray film into three substantially equal sections 88-90 so that each section 88-90 is approximately 14"×5.7". As shown in FIG. 1 and partially in FIG. 4, markers 85-87 are etched or marked on one or both sides of carriage 22 to indicate the centers of sections 88-90 as aids for visual alignment. Alternatively, division lines demarcating sections 88-90 may be etched on carriage 22.

The method steps are as follows. Position the patient on X-ray apparatus 10 with his head near the "head" end of x-ray apparatus 10. Prior to fully draping the patient for surgery, turn manual turn wheel 62 either clockwise or counterclockwise, depending on the present location of carriage 22, to position the first section of carriage 22 to approximately align marker 87 with the hips of the patient. Alignment is done visually by viewing carriage 22 through the transparent side panel 15 or 19 of X-ray apparatus 10. Note the reading of indicator 66. Advance carriage 22 further down X-ray apparatus 10 and approximately align marker 86 with the knees of the patient, so that the knees are directly above the middle section 89 of carriage 22. Again note the reading of indicator 66. Advance carriage 22 to approximately align marker 85 with the centers of the patient's ankles, and note the indicator reading.

Immediately after the placement of the trial prosthetic components, a determination can be made as to whether the procedure was successful by taking three X-rays of hips, knees and ankles successively on the 14"×17" film. This is achieved by the following steps. If an X-ray film cassette containing an X-ray film has not been loaded through end opening 54, it is loaded. Close door 56. Manipulate turn wheel 62 so that the first indicated reading for the hips x-ray obtained earlier is reached. The first section, or section 88 of X-ray film, as indicated in FIG. 5, should be approximately but sufficiently accurately aligned with the hips of the patient. An X-ray source (not shown) is aligned therewith and an exposure is made of the hips on the first section 88 of the film. Manual turn wheel 62 is rotated again so that the second indicated reading is reached. A second exposure is made of the knees on the second section 89 of the film. Carriage 22 is again transported and aligned so that the third reading is obtained on indicator 66. A third exposure is made of the ankles on the third section 90 on the film. It is obvious that the patient is not moved between each of these exposures. Other known precautions associated with X-ray taking should also be observed.

Accordingly, after development, a composite X-ray image such as that shown in FIG. 5 is obtained. The resultant X-ray image contains crisp images of the hips, knees and ankles 92-96 with a slight blurring near section dividing lines due to multiple exposures to X-rays. On the image, centers of femoral heads 100 and 101, prosthetic implant 103 and knee 104, and ankles 106 and 107 of the leg or legs are located and marked. Lines 200 or 201 are drawn to connect the center of femoral head 100 or 101 and the center of ankle 106 or 107 of each leg. As shown, line 200 falls on the center of the trial prosthetic implant 103. However, line 201 falls medially of the center of the knee, which is defined as the intercondylar notch of the femur and the spines of the tibia in the knee and indicated by marking 104. Therefore FIG. 5 shows that the trial implant drammatically improved the alignment of the "knee" with respect to the hips and ankle, as contrasted with the misaligned knee 94.

The X-ray taking procedure described above may also be repeated to determine whether any corrective procedure has been performed successfully. Because the alignment readings are already available, the X-rays can be repeated quickly without substantial loss of time. Therefore, it can be seen that accurate positioning and alignment of the X-ray film and repeatability of the X-rays are possible with the preferred embodiment of the present X-ray apparatus and method.

Although the present invention has been described in detail, it should be understood that various changes, substitutions and alterations can be made thereto without departing from the spirit and scope of the present invention as defined by the appended claims.

What is claimed is:

1. X-ray apparatus for supporting a patient and disposed on a table, comprising:

a housing having a top panel for supporting said patient and a bottom panel coupled to and spaced from said top panel for interfacing with said table;

a frame mounted in said housing for receiving and transporting an X-ray film cassette;

drive means mounted in said housing and coupled to said frame for slidably displacing said frame longitudinally substantially the length of said housing; and means coupled to said drive means for accurately indicating the position of said frame along the length of said housing.

2. The X-ray apparatus, as set forth in claim 1, further comprising a track longitudinally disposed within said housing and extending substantially the length thereof, said track adapted for receiving and supporting said frame.

3. The X-ray apparatus, as set forth in claim 2, wherein said frame comprises at least two wheels for traveling longitudinally along said track, said track adapted for receiving and supporting said wheels.

4. The X-ray apparatus, as set forth in claim 3, further comprising a second track disposed parallel and spaced from said track.

5. The X-ray apparatus, as set forth in claim 4, wherein said frame comprises at least four wheels for rolling longitudinally along both said tracks.

6. The X-ray apparatus, as set forth in claim 1, further comprising means for accessing said X-ray film cassette carried in said frame.

7. The X-ray apparatus, as set forth in claim 1, wherein said housing further comprises substantially vertical side panels, at least one of said side panels defining an opening for allowing mounting and removal of said X-ray film cassette.

8. The X-ray apparatus, as set forth in claim 7, wherein said housing further comprises a door for selectively covering and revealing said opening.

9. The X-ray apparatus, as set forth in claim 1, wherein said drive means comprises:

a first shaft mounted substantially horizontally and transversely at a first end of said housing;

a first pulley mounted on one end of said first shaft;

a second shaft mounted substantially horizontally and transversely at a second end of said housing;

a second pulley mounted on one end of said second shaft; and a belt attached to said frame and further installed around said first and second pulleys for effecting longitudinal slidable displacement of said frame.

10. The X-ray apparatus, as set forth in claim 9, wherein said drive means further comprises manual turning means coupled to said first pulley for rotatively driving said first pulley.

11. The X-ray apparatus, as set forth in claim 10, wherein said accurate position indicating means comprises a displacement indicator for indicating a relative displacement of said frame in response to rotating said manual turning means.

12. The X-ray apparatus, as set forth in claim 10, wherein said drive means further comprises:

a drive pulley mounted within said housing and coupled to said manual turning means; and a second belt coupling said drive pulley and said first pulley, so that said first pulley rotates in response to said drive pulley being rotated by said manual turning means.

13. The X-ray apparatus, as set forth in claim 12, wherein said manual turning means comprises a circular wheel.

14. The X-ray apparatus, as set forth in claim 11, wherein said accurate position indicating means comprises:

a circular face having a first plurality of division markers indicated thereon along its circumference; and a first pointer for pointing to said plurality of division markers in response to the amount of angular displacement of said manual turning means.

15. The X-ray apparatus, as set forth in claim 14, wherein said accurate position indicating means further comprises:

a second plurality of division markers indicated along the circumference of said circular face; and a second pointer for pointing to said second plurality of division markers in response to the amount of angular displacement of said manual turning means.

16. The X-ray apparatus, as set forth in claim 1, wherein said housing comprises a frame structure including said top and bottom panels and corner supports therebetween for allowing visual alignment of said X-ray film cassette frame with a portion of said patient's body.

17. The X-ray apparatus, as set forth in claim 1, wherein said housing comprises substantially vertical and transparent side panels secured between said top and bottom panels for allowing visual alignment of said X-ray film cassette frame with a portion of said patient's body.

18. The X-ray apparatus as set forth in claim 1, wherein said accurate position indicating means is mounted externally of said housing at one end thereof.

19. The X-ray apparatus, as set forth in claim 1, wherein said accurate position indicating means includes an indicator displaying the relative positioning of said frame.

20. The X-ray apparatus, as set forth in claim 1, wherein said frame receives and transports at least one X-ray film.

21. The X-ray apparatus, as set forth in claim 20, wherein said frame receives and transports a 14"×17" X-ray film.

22. The X-ray apparatus, as set form in claim 1, wherein said frame further comprises at least one marker for aiding visual alignment of said frame with said patient.

23. An X-ray apparatus for accurate positioning of an X-ray film cassette beneath a patient, comprising:

an upper surface for supporting said patient;

a frame for horizontally receiving and carrying said X-ray film cassette slidably mounted beneath said upper surface;

drive means coupled to said frame for slidably transporting said frame beneath said upper surface;

means coupled to said drive means for accurately actuating said drive means to position said frame at a plurality of predetermined locations beneath said upper surface; and indicator means coupled to said accurate actuating means for indicating the relative position of said X-ray film cassette frame.

24. The X-ray apparatus, as set forth in claim 23, wherein said drive means comprises:

a first and second pulley mounted longitudinally spaced from one another; and a belt attached to said X-ray film cassette frame and wound around said first and second pulleys, the rotation of one pulley effecting the rotation of the other pulley and linear displacement of said X-ray film cassette frame.

25. The X-ray apparatus, as set forth in claim 23, wherein said drive means comprises:

a first and second pulley mounted longitudinally spaced from one another;

a third and fourth pulley mounted longitudinally spaced from one another and spaced from said first and second pulleys; and a first belt attached to said X-ray film cassette frame and wound around said first and second pulleys; and a second belt attached to said X-ray film cassette frame and wound around said third and fourth pulleys, the rotation of said first pulley effecting a synchronous rotation of said third pulley, the rotation of said first and third pulleys effecting the rotation of said second and fourth pulleys through s id first and second belts and a linear displacement of said X-ray film cassette frame.

26. The X-ray apparatus, as set forth in claim 23, wherein said frame comprises at least two wheels.

27. The X-ray apparatus, as set forth in claim 26, further comprising at least one track longitudinally disposed beneath said upper surface for receiving said wheels.

28. The X-ray apparatus, as set forth in claim 23, wherein said frame comprises four wheels, said apparatus further including two parallely spaced tracks longitudinally disposed beneath said upper surface for receiving said wheels.

29. The X-ray apparatus, as set forth in claim 23, wherein said actuating means comprises a manual turn wheel coupled to said drive means for effecting a longitudinal linear displacement of said X-ray film cassette frame.

30. The X-ray apparatus, as set forth in claim 24, wherein said actuating means comprises:

a manual turn wheel;

a driving pulley coupled to said manual turn wheel for synchronous angular displacement;

a driving belt coupling said driving pulley and said first pulley, the angular displacement of said manual turn wheel effecting a linear displacement of said X-ray film cassette frame.

31. The X-ray apparatus, as set forth in claim 23, wherein said indicator means comprises:

a circular dial having a plurality of divisions; and at least one pointer for pointing to one of said plurality of divisions, said plurality of divisions representative of the relative position of said X-ray film cassette frame.

32. The X-ray apparatus, as set forth in claim 23, further comprising a generally rectangular housing, said housing having substantially vertical side panels, at least one of said side panels being transparent, said housing defining at least one end opening for allowing access of said X-ray film cassette.

33. The X-ray apparatus, as set forth in claim 32, wherein said housing further comprises an end door for selectively covering or revealing said end opening.

34. Apparatus for supporting a patient and use with X-ray equipment, comprising:

a substantially horizontal and elongated top panel for supporting said patient;

a substantially horizontal and elongated bottom panel mounted parallel with and spaced from said top panel, said top and bottom panels defining a cavity;

at least one channel disposed longitudinally on said bottom panel in said cavity, said channel extending substantially the length of said top and bottom panels;

a carrier having at least two wheels for traveling along said channel, said carrier adapted for carrying a cassette containing at least one X-ray film;

a drive system coupled to said carrier for slidably transporting said carrier longitudinally substantially the length of said top and bottom panels; and an indicator coupled to said drive system and mounted externally of said cavity for displaying a value indicative of the position of said carrier.

35. The apparatus, as set forth in claim 34, wherein said top and bottom panels are substantially rectangular.

36. The apparatus, as set forth in claim 35, further comprising two vertical, elongated and substantially transparent side panels joining said top and bottom panels.

37. The apparatus, as set forth in claim 36, further comprising:

a first end panel joining said top, bottom, and side panels;

a second end panel detachably joining said top, bottom, and side panels for providing an opening to said cavity.

38. The apparatus, as set forth in claim 37, wherein said second end panel is connected to one of said top, bottom and side panels.

39. The apparatus, as set forth in claim 34, wherein said top panel is permeable to X-rays.

40. The apparatus, as set forth in claim 34, wherein said drive system comprises:

a first pulley rod mounted transversely in said cavity near said first end panel;

a first pulley mounted on said first pulley rod;

a second pulley rod mounted transversely in said cavity near said second end panel;

a second pulley mounted on said second pulley rod; and a belt attached to said carrier and installed around said first and second pulleys.

41. The apparatus, as set forth in claim 40, wherein said drive system further comprises a belt tensioner coupled to said belt for maintaining tension in said belt.

42. The apparatus, as set forth in claim 40, wherein said drive system further comprises actuating means for rotating said first pulley and effecting linear travel of said carrier along said channel.

43. The apparatus, as set forth in claim 42, wherein said actuating means comprises:

a drive rod mounted transversely near said first pulley rod;

a drive pulley mounted on said drive rod;

a drive belt substantially tightly installed around said first pulley and said drive pulley; and a manual turn wheel coupled to said drive pulley for effecting angular displacement of said drive pulley in response to said manual turn wheel being rotated.

44. The apparatus, as set forth in claim 43, wherein said indicator includes:

means for measuring said angular displacement of said manual turn wheel; and means for displaying said measured angular displacement.

45. The apparatus, as set forth in claim 44, wherein said displayed angular displacement is indicative of relative linear travel of said carrier.

46. A method for taking X-rays of a patient lying on a horizontal surface during a medical procedure, comprising the steps of:
   actuating a drive mechanism for positioning an X-ray film cassette beneath the patient and aligning with a preselected body part;
   noting the relative position of said X-ray film cassette indicated by position indicating means;
   actuating said drive mechanism for repositioning said X-ray film cassette and aligning with a second preselected body part;
   noting a relative position of said X-ray film cassette indicated by said position indicating means;
   repeating said above steps until alignment relative positions have been obtained for all body parts to be X-rayed;
   performing said medical procedure;
   actuating said drive mechanism until the relative position of said X-ray film cassette for the preselected body part is reached as indicated by said position indicating means;
   taking an X-ray of said preselected body part; and
   repeating the above two steps until all preselected body parts have been X-rayed.

47. A method of X-raying a patient, comprising the steps of:
   apportioning an X-ray film into at least two sections;
   supporting said patient on a surface permeable to X-rays;
   providing an X-ray film cassette carrying said X-ray film under said first surface;
   selecting a predetermined number of portions of said patient's body for taking X-rays;
   slidably transporting said X-ray film cassette to achieve alignment of a predetermined apportioned section of said film cassette with a first selected portion of said patient's body;
   taking an X-ray of said first selected body portion;
   slidably transporting said X-ray film cassette to achieve alignment of another predetermined apportioned and unexposed section of said film cassette with another selected portion of said patient's body;
   taking an X-ray of said other selected body portion; and
   repeating said above two steps until X-rays have been taken of all selected portions of said patient's body.

48. The method, as set forth in claim 47, further comprising the step of selecting for X-ray taking said patient's hips, knees and ankles.

49. The method, as set forth in claim 48, wherein said X-ray film apportioning step includes the step of apportioning said X-ray film into first, second and third equal sections.

50. The method, as set forth in claim 49, wherein said slidably transporting steps include the steps of slidably transporting said X-ray film cassette to achieve alignment of said first X-ray film section with said hips, said second X-ray film section with said knees, and said third X-ray film section with said ankles.

51. The method, as set forth in claim 50, wherein said X-ray taking steps include exposing said first, second and third sections of said apportioned X-ray film to X-rays passing through said hips, knees, and ankles, respectively.

52. The method, as set forth in claim 51, further comprising the steps of:
   developing said X-ray film;
   drawing a line on said developed X-ray film connecting a point on said hip to a point on said ankle of the same leg; and
   determining the alignment of said knee by assessing whether said line falls near the center of said knee.

53. A method of taking X-rays of a patient's hips and knee and ankle of the same leg for determining the alignment of said knee with respect to said hips and ankle, the method comprising the steps of:
   providing a surface permeable to X-rays and supporting the patient thereon;
   providing an X-ray film cassette carrier controllably actuatable to slide under said surface and the patient's body;
   loading an X-ray film cassette carrying an X-ray film into said carrier;
   apportioning said carrier into first, second and third sections;
   controllably actuating said carrier to achieve substantial alignment of said patient's hips with said first film section;
   positioning an X-ray source generally above said patient's hips and taking an X-ray thereof;
   controllably actuating said carrier to achieve substantial alignment of said patient's knee with said second film section;
   positioning said X-ray source generally above said patient's knee and taking an X-ray thereof;
   controllably actuating said carrier to achieve substantial alignment of said patient's ankle with said third film section;
   positioning said X-ray source generally above said patient's ankle and taking an X-ray thereof;
   obtaining a developed X-ray image of said X-ray film;
   drawing a line between a corresponding hip of said hips and said ankle; and
   determining alignment of said knee by assessing whether said line falls near the center of said knee.

54. The method, as set forth in claim 53, wherein said knee is a trial knee prosthetic implant.

* * * * *

UNITED STATES PATENT AND TRADEMARK OFFICE
CERTIFICATE OF CORRECTION

PATENT NO. : 5,222,115
DATED : June 22, 1993
INVENTOR(S) : Highgenboten

It is certified that error appears in the above-identified patent and that said Letters Patent is hereby corrected as shown below:

Column 10, line 47, after "as set", delete "form" and insert --forth--.

Column 11, line 24, delete "s id", and insert --said--.

Signed and Sealed this

Fourteenth Day of June, 1994

Attest:

BRUCE LEHMAN

Attesting Officer        Commissioner of Patents and Trademarks